US008861672B2

(12) United States Patent
Maltz et al.

(10) Patent No.: US 8,861,672 B2
(45) Date of Patent: Oct. 14, 2014

(54) PATIENT POSITIONING SYSTEM

(75) Inventors: Jonathan S. Maltz, Oakland, CA (US);
Supratik Bose, Walnut Creek, CA (US);
Ali Bani-Hashemi, Walnut Creek, CA (US);
Ajay Paidi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 306 days.

(21) Appl. No.: 13/298,189

(22) Filed: Nov. 16, 2011

(65) Prior Publication Data

US 2013/0121457 A1    May 16, 2013

(51) Int. Cl.
*A61B 6/03* (2006.01)
*A61B 6/00* (2006.01)
*A61N 5/10* (2006.01)

(52) U.S. Cl.
CPC ....... *A61N 5/1049* (2013.01); *A61N 2005/1061* (2013.01); *A61B 6/488* (2013.01); *A61B 6/032* (2013.01); *A61N 2005/105* (2013.01); *A61B 6/5223* (2013.01)
USPC ................................... 378/4; 378/62; 378/65

(58) Field of Classification Search
CPC .... A61N 5/1069; A61N 5/107; A61N 5/1049
USPC ................................................. 378/4, 62, 65
See application file for complete search history.

(56) References Cited

U.S. PATENT DOCUMENTS

| | | | |
|---|---|---|---|
| 6,222,544 | B1 | 4/2001 | Tarr et al. |
| 6,535,574 | B1 | 3/2003 | Bani-Hashemi et al. |
| 7,415,095 | B2 * | 8/2008 | Wofford et al. ................. 378/65 |
| 2003/0083562 | A1 | 5/2003 | Bani-Hashemi et al. |
| 2004/0122311 | A1 * | 6/2004 | Cosman ........................ 600/427 |

FOREIGN PATENT DOCUMENTS

WO    WO 99/40846    8/1999

OTHER PUBLICATIONS

Kang, et al., *Accurate positioning for head and neck cancer patients using 2D and 3D image guidance*, Journal of Applied Clinical Medical Physics, vol. 12 No. 1, (2011), 10 pages.
Ma, et al., *In-room CT Techniques for image-guided radiation therapy*, Medical Dosimetry, vol. 31 No. 1, 2006, © 2006 American Association of Medical Dosimetrists (pp. 30-39, 10 pages total).
Lei Dong, Ph.D., *In-room CT imaging conventional CT*, (no date), University of Texas M.D. Anderson Cancer Center, Houston, TX, 81 pages.
Uematsu, et al. *A dual computed tomography linear accelerator unit for stereotactic radiation therapy: a new approach without cranially fixated stereotactic frames*, Int. J. Radiation Oncology Biology Physics, vol. 35, No. 3, 1996, © 1996 Elsevier Science Inc., SSDI:0360-3016(95)00293-3, pp. 587-592, 6 pages total.
Jans, et al., *3D interfractional patient position verification using 2D-3D registration of orthogonal images*, Medical Physics, vol. 33, No. 5, May 2006, © 2006 Am. Assoc. Phys. Med (pp. 1420-1439, 20 pages total.
Girouard, et al., *Automatic setup deviation measurements with electronic portal images for pelvic fields*, Medical Physics, vol. 35, No. 7, Jul. 1998.

* cited by examiner

Primary Examiner — Hoon Song
Assistant Examiner — Danielle Fox

(57) ABSTRACT

A system includes acquisition of a three-dimensional computed tomography image of a patient volume at a computed tomography scanner, acquisition of projection images of the patient volume located at an isocenter of a linear accelerator, and determination of a transformation between a coordinate system of the linear accelerator and a coordinate system of the three-dimensional computed tomography image based on the projection images.

9 Claims, 10 Drawing Sheets

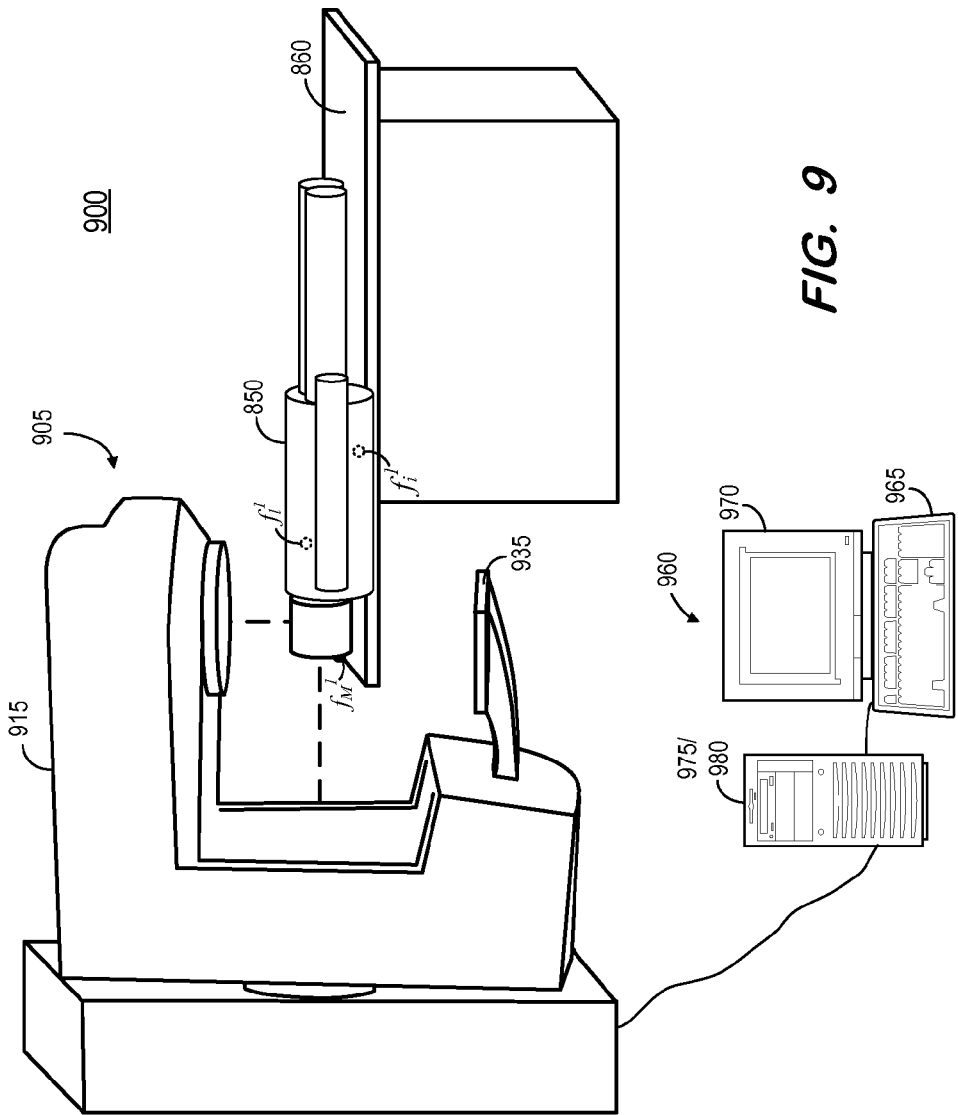

PATIENT POSITIONING SYSTEM

BACKGROUND

1. Field

The embodiments described below relate generally to the delivery of therapeutic radiation to a patient. More specifically, some embodiments are directed to the positioning of a patient volume prior to the delivery of radiation therapy.

2. Description

According to conventional radiation therapy, a beam of radiation is directed toward a target volume (e.g., a cancerous tumor) located within a patient. The radiation beam delivers a predetermined dose of therapeutic radiation to the target volume according to an established treatment plan. The delivered radiation kills cells of the target volume by causing ionizations within the cells or other radiation-induced cell damage.

Treatment plans are designed to deliver a particular radiation dose to a target volume, while ensuring that surrounding healthy tissue does not receive an unsafe dose. To design a radiation treatment plan, a designer views a three-dimensional image of a patient volume (i.e., a "planning" image) and defines one or more treatment beams to be delivered to the volume by a linear accelerator (linac), with each beam having a delivery angle, a shape, a dose rate and other characteristics. The designer also defines a treatment isocenter within the volume through which the treatment beams pass.

A treatment plan therefore assumes that relevant portions of a patient will be in particular positions relative to a linac during delivery of the treatment radiation. Therefore, the goals of the treatment plan may not be achieved if the relevant portions are not positioned in accordance with the treatment plan during actual delivery of the radiation. More specifically, errors in positioning the patient can cause the delivery of low radiation doses to tumors and high radiation doses to sensitive healthy tissue. The potential for misdelivery increases with increased positioning errors.

Many techniques have been developed to verify patient positioning prior to the delivery of treatment radiation by a linac. Specifically, this verification is intended to confirm that the treatment isocenter of the planning image is aligned with the isocenter of the linac.

According to one currently-used positioning system, tattoo marks are placed on a patient during acquisition of the planning image. The tattoo marks provide an external indication of the location of the treatment isocenter as defined by the treatment plan. Prior to treatment, radio-opaque seeds are placed on the tattoo marks and another three-dimensional image (i.e., a "pre-treatment image") is acquired, in which the seeds are visible.

The patient is then positioned for treatment by aligning the seeds/tattoos with lasers inside the linac treatment room. The lasers define the linac isocenter, so, by referring to the locations of the seeds in the pre-treatment image, it is possible to identify the linac isocenter within the pre-treatment image. Rigid registration between the planning image and the pre-treatment image provides the location of the treatment isocenter within the pre-treatment image, thereby allowing computation of the offset between the linac isocenter and the treatment isocenter. The patient is moved according to this offset and treatment commences.

The foregoing process presents several problems. First, the tasks of accurately securing the seeds on the tattoo marks and aligning the seeds with the in-room lasers are time-consuming. Moreover, both of these tasks are subject to human error. Accuracy of the process also depends on precise calibration between the in-room lasers might and the linac isocenter.

Improved patient positioning and verification systems are desired.

SUMMARY

To address at least the foregoing, some embodiments provide a system, method, apparatus, and means to acquire a three-dimensional computed tomography image of a patient volume at a computed tomography scanner, acquire projection images of the patient volume located at an isocenter of a linear accelerator, and determine a transformation between a coordinate system of the linear accelerator and a coordinate system of the three-dimensional computed tomography image based on the projection images.

In some aspects, determination of the transformation includes calculation, for each acquired projection image, of corresponding projection images from the three-dimensional computed tomography image, and determination of the transformation based on differences between the calculated projection images and their corresponding acquired projection images. Additionally, a second three-dimensional computed tomography image of the patient volume may be initially acquired, a treatment isocenter in the second three-dimensional computed tomography image identified, a second transformation between the coordinate system of the three-dimensional computed tomography image and the coordinate system of the second three-dimensional computed tomography image determined, a position of the treatment isocenter in the second three-dimensional computed tomography image determined based on the transformation and the second transformation, and the treatment isocenter in the patient volume aligned with the linac isocenter based on the determined positions.

According to some aspects, acquisition of the three-dimensional computed tomography image of the patient volume includes acquisition of the three-dimensional computed tomography image of the patient volume positioned on a support comprising fiducials, and acquisition of the projection images of the patient volume located at the isocenter of the linear accelerator includes acquisition of the projection images of the patient volume positioned on the support. Moreover, determination of the transformation includes determination of first positions of the fiducials in the coordinate system of the three-dimensional computed tomography image, determination of second positions of the fiducials in the coordinate system of the linear accelerator based on the projection images, and determination of the transformation based on the first positions and the second positions.

The claims are not limited to the disclosed embodiments, however, as those in the art can readily adapt the description herein to create other embodiments and applications.

BRIEF DESCRIPTION OF THE DRAWINGS

The construction and usage of embodiments will become readily apparent from consideration of the following specification as illustrated in the accompanying drawings, in which like reference numerals designate like parts, and wherein:

FIG. 9 is a perspective view of a radiation treatment room according to some embodiments;

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
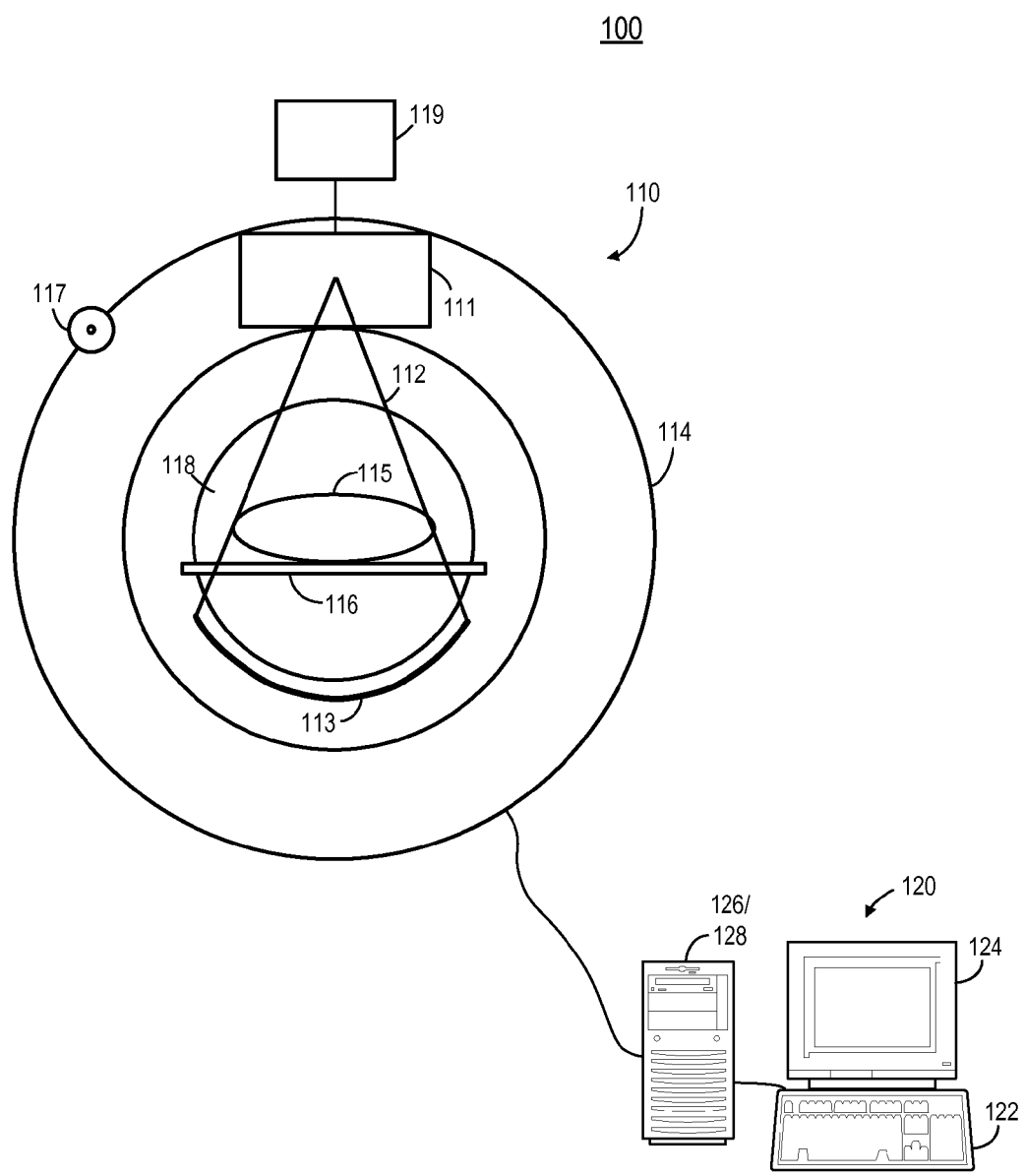
FIG. 1 illustrates a computed tomography system according to some embodiments.

FIG. 1 illustrates CT scanner 110 is located in CT room 100. CT scanner 110 includes X-ray source 111 for emitting fan-shaped X-ray beam 112 toward radiation receiver 113. Both X-ray source 111 and radiation receiver 113 are mounted on ring 114 such that they may be rotated through 360 degrees while maintaining the physical relationship therebetween.

In operation, patient 115 is positioned on bed 116 to place a portion of patient 115 between X-ray source 111 and radiation receiver 113. Next, X-ray source 111 and receiver 113 are rotated by rotation drive 117 around cavity 118 in which patient 115 lies. During this rotation, X-ray source 111 is powered by high-voltage generator 119 to transmit X-ray radiation toward receiver 113. Receiver 113 receives the radiation and produces a set of data (i.e., a projection image) for each projection angle.

Operator console 120 includes input device 122 for receiving instructions from an operator and output device 124, which may be a monitor for presenting operational parameters of scanner 110 and for displaying images acquired thereby. Input device 122 and output device 124 are coupled to processor 126 and storage 128. Processor 126 may execute program code stored in storage 128 to perform any of the operations, and/or to cause scanner 110 to perform any of the operations, described herein.

Processor 126 may execute program code of storage 128 to reconstruct three-dimensional images from the projection images acquired by scanner 110. Processor 126 may also allow an operator to view, on display 124, "slices" of such three-dimensional images. Processor 126 may also execute program code of storage 128 to allow an operator to identify a treatment isocenter within patient 115, and to create a treatment plan as is known in the art. According to some embodiments, a separate computer system including a processor (e.g., a dedicated planning system) may execute program code to generate treatment plans as described herein.

Figure 2:
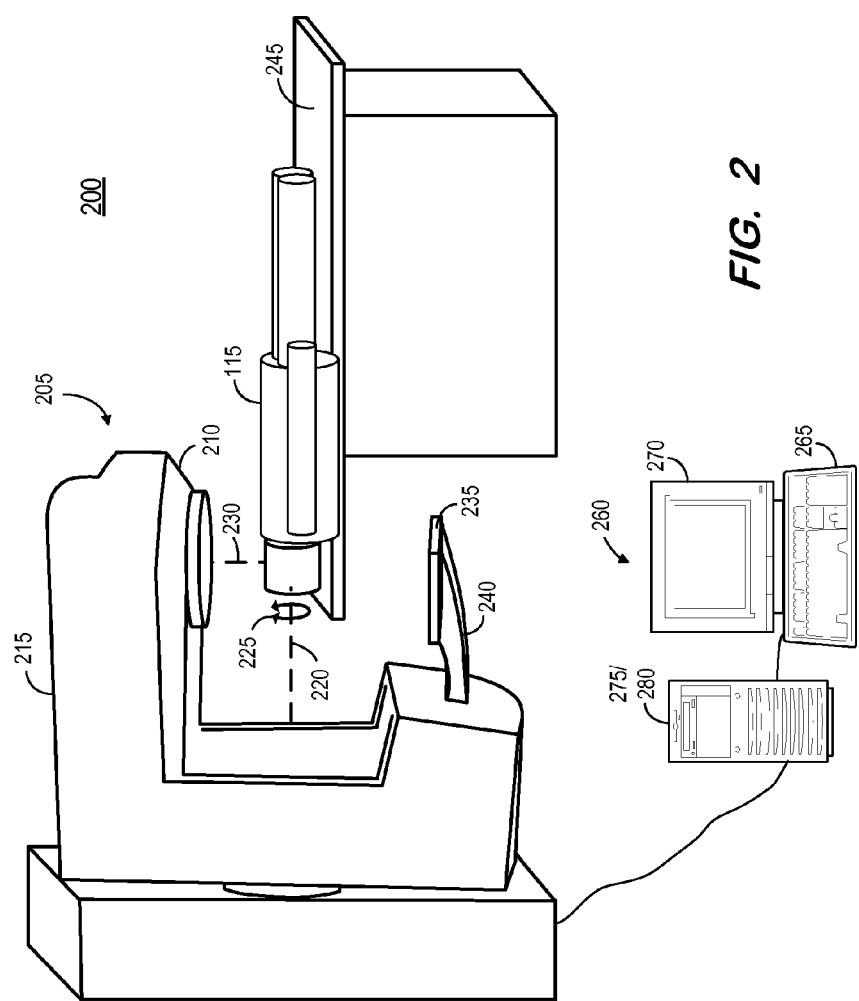
FIG. 2 is a perspective view of a radiation treatment room according to some embodiments.

FIG. 2 illustrates radiation treatment room 200 pursuant to some embodiments. Radiation treatment room 200 includes linac 205, table 245 and operator console 260. The elements of radiation treatment room 200 may be used to deliver radiation to a target volume of patient 115. In this regard, patient 115 may comprise a patient of whom three-dimensional images were previously generated by CT scanner 110.

Linac 205 generates and emits radiation beams, and is primarily composed of treatment head 210 and gantry 215. Treatment head 210 includes a beam-emitting device (not shown) for emitting one or more radiation beams during treatment, calibration, and/or other scenarios. An emitted radiation beam may comprise electron, photon or any other type of radiation. According to some embodiments, the radiation beam exhibits energies of more than 1 MeV (i.e., megavoltage radiation) and/or between 50 and 150 keV (i.e., kilovoltage radiation). Also included within treatment head 210 is a beam-shielding device, or collimator (not shown), for shaping the beam according to a treatment plan.

Treatment head 210 is coupled to a projection of gantry 215. Gantry 215 is rotatable around gantry axis 220 before, during and after radiation treatment. As indicated by arrow 225, gantry 215 may rotate clockwise or counter-clockwise according to some embodiments. Rotation of gantry 215 serves to rotate treatment head 210 around axis 220.

During radiation treatment, a radiation beam is emitted from treatment head 210 as a divergent beam (i.e., a cone). The beam is emitted towards an isocenter of linac 205. The isocenter is located at the intersection of beam axis 230 and gantry axis 220. Due to divergence of the radiation beam and the shaping of the beam by the aforementioned beam-shaping devices, the beam may deliver radiation to a volume of patient 115 rather than only to the isocenter.

During treatment, linac 205 may be operated so that each treatment beam emitted thereby exhibits a desired intensity (e.g., represented in monitor units (MU)) and aperture (i.e., a cross-sectional shape determined at least in part by the above-mentioned collimator), and is delivered from a desired gantry angle. The intensity, aperture and gantry angle of a beam are specified by a treatment plan, and control software may configure linac 205 to automatically execute such a treatment plan by delivering beams of the desired intensities and shapes from the desired angles at desired moments.

Table 245 supports patient 115 during radiation treatment. Table 245 may be adjustable to assist in positioning a treatment area of patient 115 at the isocenter of linac 205. Table 245 may also be used to support devices used for such positioning, for calibration and/or for verification.

Imaging device 235 may acquire images before, during and/or after radiation treatment. For example, imaging device 235 may be used to acquire images for verification and recordation of a target volume position and of an internal patient portal to which radiation is delivered.

Imaging device 235 may be attached to gantry 215 in any manner, including via extendible and retractable housing 240. Rotation of gantry 215 may cause treatment head 210 and imaging device 235 to rotate around the isocenter such that isocenter remains located between treatment head 210 and imaging device 235 during the rotation.

Imaging device 235 may comprise any system to acquire an image based on received megavoltage photon radiation. In a case that linac 205 is capable of producing kilovoltage photon radiation via beamline modification or other techniques, imaging device 235 may also acquire images based on such kilovoltage radiation. In some embodiments, imaging device 235 is a flat-panel imaging device using a scintillator layer and solid-state amorphous silicon photodiodes deployed in a two-dimensional array. In operation, the scintillator layer receives photons and generates light in proportion to the intensity of the received photons. The array of photodiodes receives the light and records the intensity of received light as stored electrical charge.

In other embodiments, imaging device 235 converts received photons to electrical charge without requiring a scintillator layer. The photons are absorbed directly by an array of amorphous selenium photoconductors. The photoconductors convert the photons directly to stored electrical charge. Imaging device 235 may also comprise a CCD or tube-based camera. Such an imaging device 235 may include a light-proof housing within which are disposed a scintillator, a mirror, and a camera.

The charge developed and stored by imaging device 235 represents radiation intensities at each location of a radiation field produced by a beam emitted from treatment head 210. Since patient 115 is located between treatment head and imaging device 235, the radiation intensity at a particular location represents the attenuative properties of tissues along a divergent line between a radiation source in treatment head 210 and the particular location. The set of radiation intensities acquired by imaging device 235 may therefore comprise a two-dimensional projection image of these tissues.

Operator console 260 includes input device 265 for receiving instructions from an operator and output device 270, which may be a monitor for presenting operational parameters of linac 205 and imaging device 235 and/or interfaces for receiving instructions. Output device 270 may also present a two-dimensional projection image, a three-dimensional megavoltage (or kilovoltage) cone beam image constructed based on several two-dimensional projection images, and/or two-dimensional "slice" images based on three-dimensional images.

Input device 265 and output device 270 are coupled to processor 275 and storage 280. Processor 275 may execute program code to perform any of the determinations and generations described herein, and/or to cause linac 205 to perform any of the process steps described herein.

Storage 280 may also store program code to generate and/or modify a treatment plan according to some embodiments. Such code may comprise the SyngoRT™ suite or the KONRAD™ treatment planning system sold by Siemens Medical Solutions®. Accordingly, storage 280 may also store radiation treatment plans in accordance with any currently- or hereafter-known format. The treatment plans may comprise scripts that are automatically executable by elements of room 200 to provide radiation therapy fractions. Each fraction of each treatment plan may require a patient to be positioned in a particular manner with respect to treatment head 210.

Operator console 260 may be in a room other than treatment room 200, in order to protect its operator from radiation. For example, treatment room 200 may be heavily shielded, such as a concrete vault, to shield the operator from radiation generated by linac 205.

Figure 3:
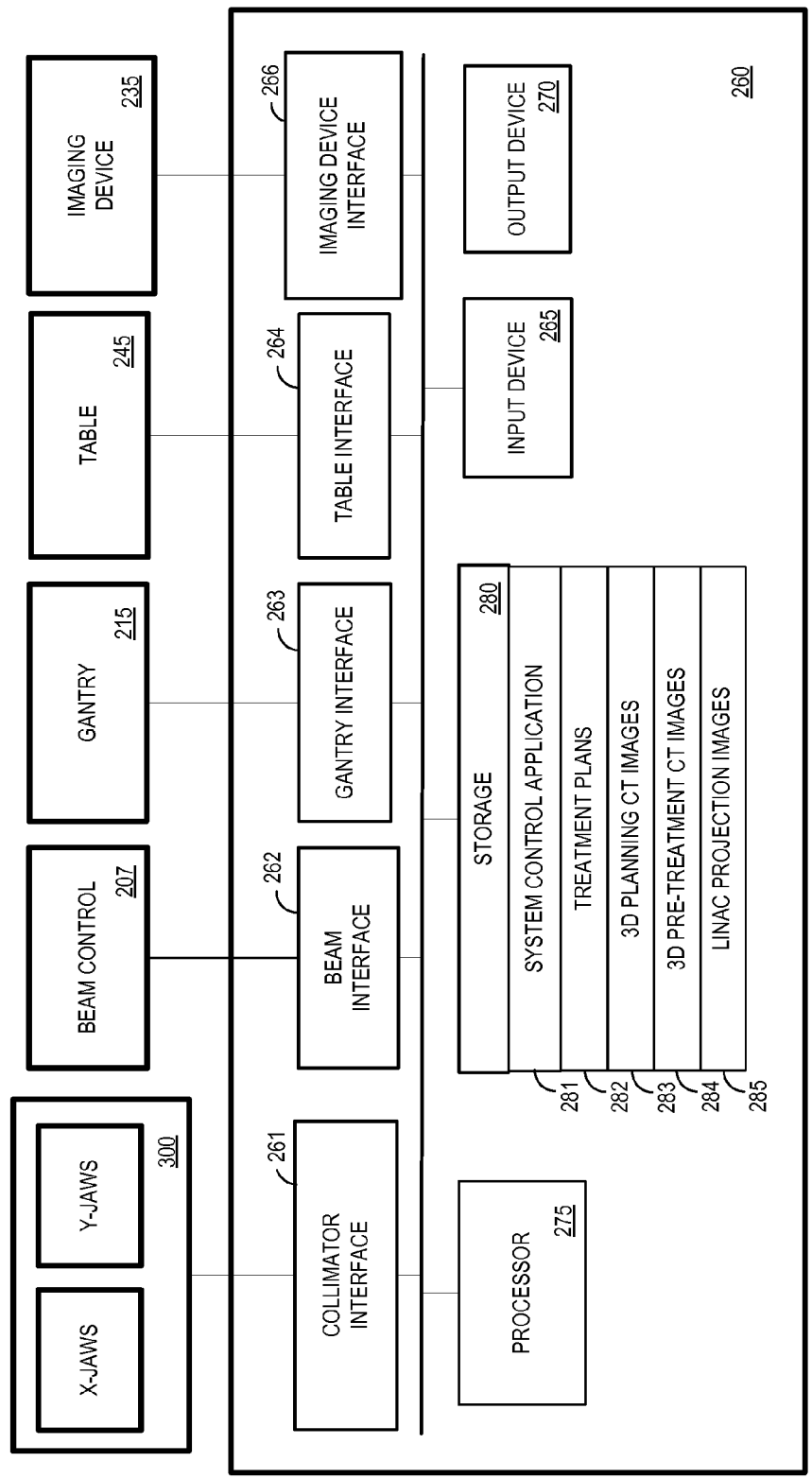
FIG. 3 is a block diagram of the internal architecture of radiation treatment room devices according to some embodiments.

FIG. 3 is a block diagram of elements of treatment system 300 according to some embodiments. The illustrated elements may be implemented by any suitable combination of hardware, software and/or firmware. Operator console 260 may be implemented by one or more separate computing systems.

As shown, operator console 260 includes several elements for interfacing with other elements of treatment system 200. Specifically, operator console 260 includes collimator interface 261, beam interface 262, gantry interface 263, table interface 264, and imaging device interface 266. Operator console 260 may control the various elements through the interfaces and based on instructions received from processor 275.

Collimator interface 261 may be used to control the opening, closing and rotation of collimator 300. Beam interface 262 may control beam-controlling elements 207 of linac 205 based on desired beam characteristics. In particular, beam interface 262 may control trigger signals for controlling an injector current and RF power signal to generate a treatment beam or an imaging beam having a particular energy.

Interfaces 261, 262, 263, 264 and 266 may comprise dedicated hardware and/or software interfaces, and one or more of interfaces 261, 262, 263, 264 and 266 may be implemented by a single interface. For example, interfaces 261 through 263 may be implemented by a single Ethernet interface and interfaces 264 and 266 may be implemented by proprietary interfaces for interfacing with table 245 and imaging device 235.

Processor 275 executes processor-executable program code stored in storage 280 to provide operation according to some embodiments. Storage 280 may comprise any tangible medium, including but not limited to a fixed disk, a floppy disk, a CD-ROM, a DVD-ROM, a Flash drive, or a magnetic tape. The program code may comprise system control application 281 to execute one of treatment plans 282 according to some embodiments.

Treatment plans 282 may conform to any currently- or hereafter-known format. Treatment plans 282 may comprise scripts that are automatically executable by linear accelerator 205 and treatment table 245 to provide radiation therapy fractions. Each of treatment plans 282 may require a patient to be positioned in a particular manner with respect to treatment head 210. In this regard, system control application 281 is executed to position a patient in conformance with a treatment plan according to some embodiments. Details of such positioning according to some embodiments will be provided below.

Storage 280 also comprises three-dimensional planning CT images 283, three-dimensional pre-treatment CT images 284 and linac projection images 285. Images 283 through 285 may be employed as described below to position a patient according to some embodiments.

A hardware environment according to some embodiments may include less or more elements than those shown in FIGS. 1 through 3. In addition, embodiments are not limited to the illustrated devices and/or to the illustrated environment.

Figure 4:
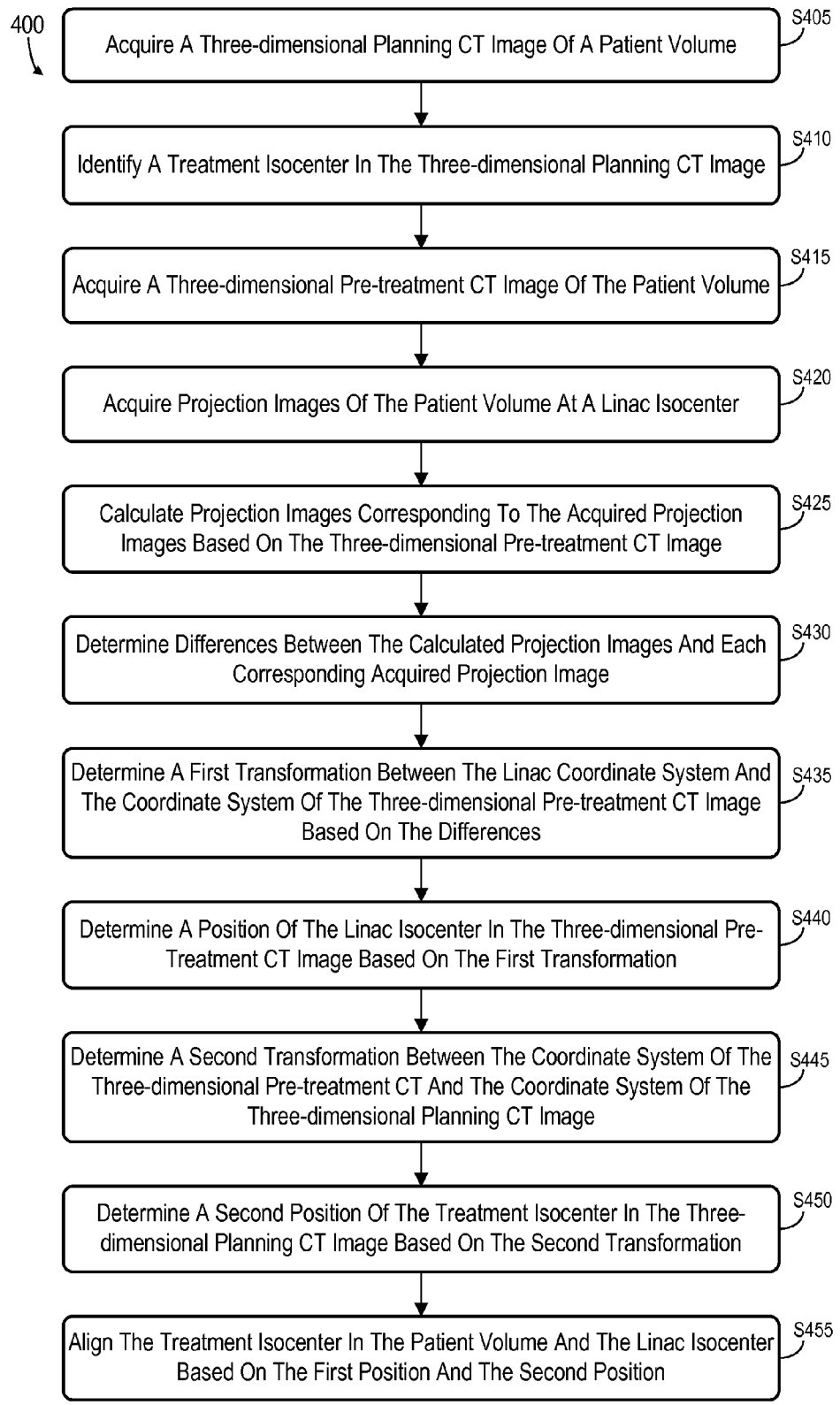
FIG. 4 comprises a flow diagram illustrating a process according to some embodiments.

FIG. 4 is a flow diagram of process 400 according to some embodiments. Process 400 and the other processes described herein may be performed using any suitable combination of hardware, software or manual means. Software embodying these processes may be stored by any tangible medium, including but not limited to a fixed disk, a floppy disk, a CD-ROM, a DVD-ROM, a Flash drive, or a magnetic tape. Examples of these processes will be described below with respect to the elements of rooms 100 and 200, but embodiments are not limited thereto.

Initially, at S405, a three-dimensional planning image of a patient volume is acquired. The three-dimensional planning image may be acquired using a CT scanner such as scanner 110, a kilovoltage or megavoltage cone beam imaging system, or by any other system. Some embodiments of S405 do not include acquisition of projection images and reconstruction of a three-dimensional image based on the projection images, but may simply include obtaining a three-dimensional planning image which was created by another entity (e.g., another hospital) in a computer-readable format.

A treatment isocenter in the three-dimensional planning CT image is identified at S410. In some embodiments, a clinician operates console 120 to evaluate the three-dimensional planning image to identify the treatment isocenter. Such evaluation may include review of two-dimensional slices of the three-dimensional planning image. In one example, the clinician locates a tumor in the three-dimensional planning image and chooses the center of the tumor as the treatment isocenter. A treatment plan may also be determined at S410 based on the treatment isocenter.

S415 through S455 may occur soon before actual execution of the treatment plan. At S415, a three-dimensional pre-treatment image of the patient volume is acquired. The three-dimensional pre-treatment image is intended to record any movement of the treatment isocenter resulting from physiological changes or the like. The three-dimensional pre-treatment image may be acquired the same scanner used at S405, a different CT scanner within the same treatment center as the scanner used at S405, or a different CT scanner within a different treatment center as the scanner used at S405.

Next, at S420, the patient volume is moved to a linac isocenter and projection images of the patient volume are obtained. Acquisition of the projection images may include rotating gantry 215 to various positions around patient 115 and, at each position, emitting radiation toward imaging device 235 to acquire a two-dimensional projection image of patient 115. At least some of the various positions may be orthogonal to one another.

According to some embodiments, and prior to S420, tattoo marks placed on patient 115 after identification of the treatment isocenter as described above are roughly aligned with lasers (not shown) within the treatment room 200 in order to roughly register the treatment isocenter with the isocenter of linac 205. Process 400, however, does not require laser-based alignment for efficacy.

Projection images corresponding to the acquired projection images are calculated at S425 based on the three-dimensional pre-treatment image. Generally speaking, S425 comprises calculating, for each gantry position, a theoretical projection image that would have been acquired if the linac isocenter and the treatment isocenter were perfectly aligned during S420. As will be described below, the calculated projection images may comprise Digitally Reconstructed Radiographs (DRRs) determined from the three-dimensional pre-treatment image. Calculation of the projection images may employ a projection matrix which uniquely maps any three-dimensional point in room 200 onto a two-dimensional point on imaging device 235.

Differences between the calculated projection images and each corresponding acquired projection image are determined at S430. That is, for each gantry position, differences are determined between a projection image acquired at that gantry position and the theoretical projection image that would have been acquired at that gantry position if the linac isocenter and the treatment isocenter were perfectly aligned.

Next, at S435, a first transformation between the linac coordinate system and the coordinate system of the three-dimensional pre-treatment image is determined based on the differences. A detailed example of this determination is provided below.

Next, at S440, a position of the linac isocenter in the three-dimensional pre-treatment image is determined based on the first transformation. In this regard, the first transformation transforms any point in the linac coordinate system to a point in the coordinate system of the three-dimensional pre-treatment image. Therefore, the transformation is used at S440 to transform the origin (i.e., (0, 0, 0)) in the linac coordinate system to a corresponding point in the coordinate system of the three-dimensional pre-treatment image.

A second transformation between the coordinate system of the three-dimensional pre-treatment image and the coordinate system of the three-dimensional planning image is determined at S445. This transformation may comprise a feature-based 3D-3D registration between the two images as is known in the art. Based on second transformation, a position of the treatment isocenter in the three-dimensional pre-treatment image is determined at S450.

Since the position of the treatment isocenter in the three-dimensional pre-treatment image and the position of the linac isocenter in the three-dimensional pre-treatment image are now known, the positions of the linac isocenter and the treatment isocenter relative to one another may be easily determined. Based on these positions, the treatment isocenter in the patient volume is aligned with the linac isocenter at S455. Alignment at S455 may comprise moving patient 115 and/or table 245 with respect to the isocenter of linac 210.

The following is a detailed description of S425 through S440 according to some embodiments. To assist in the understanding thereof, the relevant coordinate systems will initially be defined.

Figure 5:
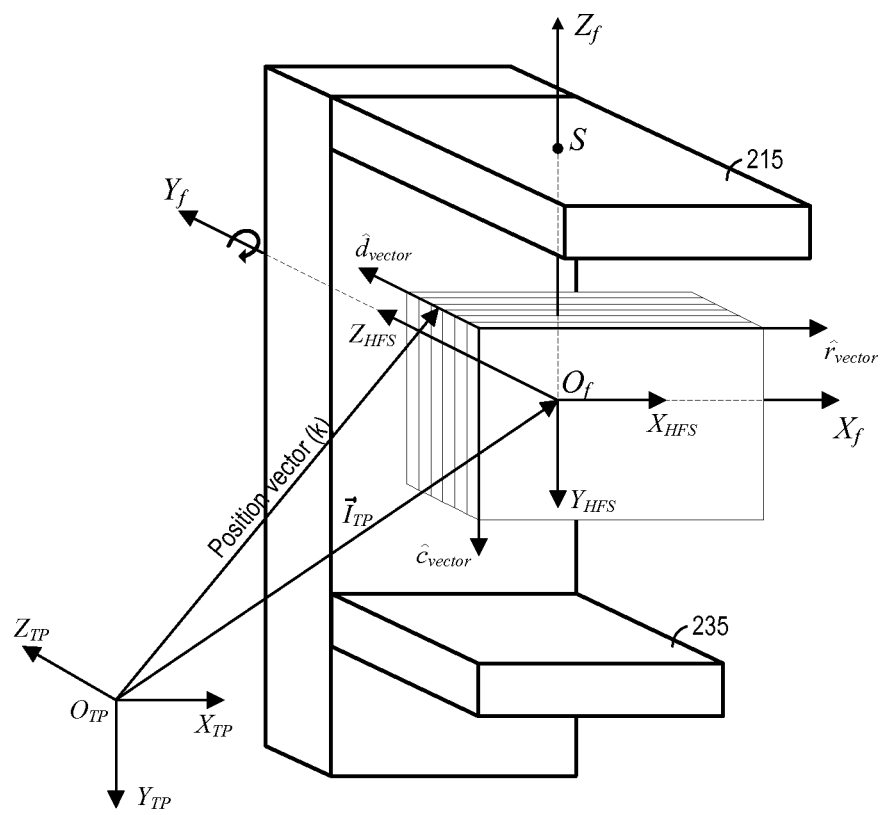
FIG. 5 illustrates various coordinate systems according to some embodiments.

FIG. 5 includes block representations of gantry 215 and imaging device 235 of linac 210. Fixed coordinate system (F) is fixed with respect to room 200, with its origin $O_F$ located at the linac isocenter. The $Z_F$ axis is oriented vertically and coincides with the central axis (CAX) of a beam produced by the gantry 215 when at the 0 degree position. The $Y_F$ axis is directed toward gantry 215 and the $X_F$ axis increases toward the right for an observer facing gantry 215.

Treatment Patient Volume coordinate system (TP) is associated with the three-dimensional pre-treatment image. Its origin $O_{TP}$ is set by the imaging device used to acquire the pre-treatment image. Axes $X_{TP}$, $Y_{TP}$ and $Z_{TP}$ follow the conventions of the fixed coordinate system. The axis $Z_{TP}$ runs in the caudocranial (feet to head) direction, the axis $Y_{TP}$ is directed from the anterior to posterior direction and the axis $X_{TP}$ increases from the right to left of the patient. The present description assumes right-handed coordinate systems. Therefore, an anticlockwise rotation around an axis, as viewed by one looking toward the origin from the positive side of the axis, is considered a positive rotation.

Each slice in the three-dimensional pre-treatment image may be defined by the following quantities in the TP system:

Row Vector: The unit row vector $r_{vector}$ runs along the row of each slice. Since the acquired slices are parallel to each other, each slice has the same row vector.

Column Vector: The unit column vector $c_{vector}$ runs along the column of each slice. Again, since the acquired slices are parallel to each other, each slice has the same column vector.

Position Vector: The position vector $POS_{vector}(k)$ describes the location of the center of the top left voxel (the first transmitted voxel) of the k-th slice in the TP system.

Voxel Location: In a CT volume, along with unit row vector $r_{vector}$, unit column vector $c_{vector}$ and position vector $POS_{vector}(k)$ for slice k, also available are information of pixel width $p_{width}$, pixel height $p_{height}$, width in number of pixels (in row direction) $N_{width}$, height in number of pixels (in column direction) $N_{height}$ and number of slices $N_{slices}$. The center of voxel(i, j, k), $1 \le i \le N_{width}$, $1 \le j \le N_{height}$, $1 \le k \le N_{slice}$, in the TP coordinate system is computed as below:

$$POS(i,j,k) = POS_{vector}(k) + (i-1)p_{width}r_{vector} + (j-1)p_{height}c_{vector}$$

If slices are acquired with equal gap and thickness, the voxel location may be alternatively computed as:

$$POS(i,j,k) = POS_{vector}(1) + (i-1)p_{width}r_{vector} + (j-1)p_{height}c_{vector} + (k-1)p_{slice}d_{vector}$$

Here, $$d_{vector} = (POS_{vector}(N_{slices}) - POS_{vector}(1))/|POS_{vector}(N_{slices}) - POS_{vector}(1)|$$

And $$p_{slice} = (POS_{vector}(N_{slices}) - POS_{vector}(1))/N_{slices} - 1$$

The coordinate transformation from a system $s_2$ to a system $s_1$ is denoted as $T_{s_1}^{s_2}$. Throughout, we use homogeneous coordinate system. Based on this notation, the transformation from the system F to system TP is denoted as $T_{TP}^F$.

FIG. 5 also shows a head-first-supine (HFS) coordinate system having an origin located at linac isocenter $O_f$. Rotation about X axis by −90 degrees, indicated as $R^c_X(-90°)$, transforms a point from the F system to an HFS-oriented system at machine isocenter.

The transformation $T_{pat\_ori}^{HFS}$ transforms points from the HFS-oriented system to a coordinate system determined by the current patient orientation with an origin at the linac isocenter $O_f$. The translation transformation $T(\vec{T}_{TP})$ expresses the point in the TP system whose origin is separated away from the linac isocenter $O_f$ by the vector $\vec{T}_{TP}$.

Combining the above, the coordinate transformation from the F to the TP system can be expressed as $$T_{TP}^F = T(\vec{T}_{TP}) T_{pat\_ori}^{HFS} R^c_X(-90°)$$

Figure 6A:
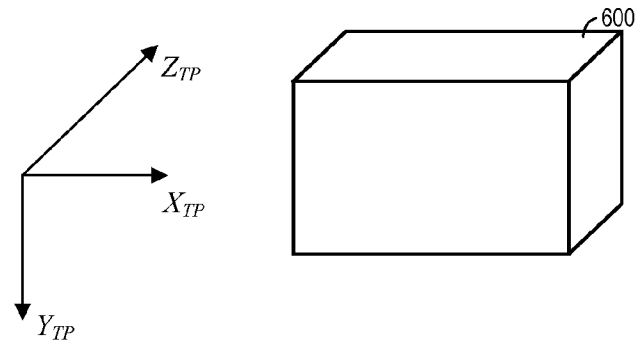
FIG. 6A illustrates a three-dimensional pre-treatment image according to some embodiments.
Figure 6B:
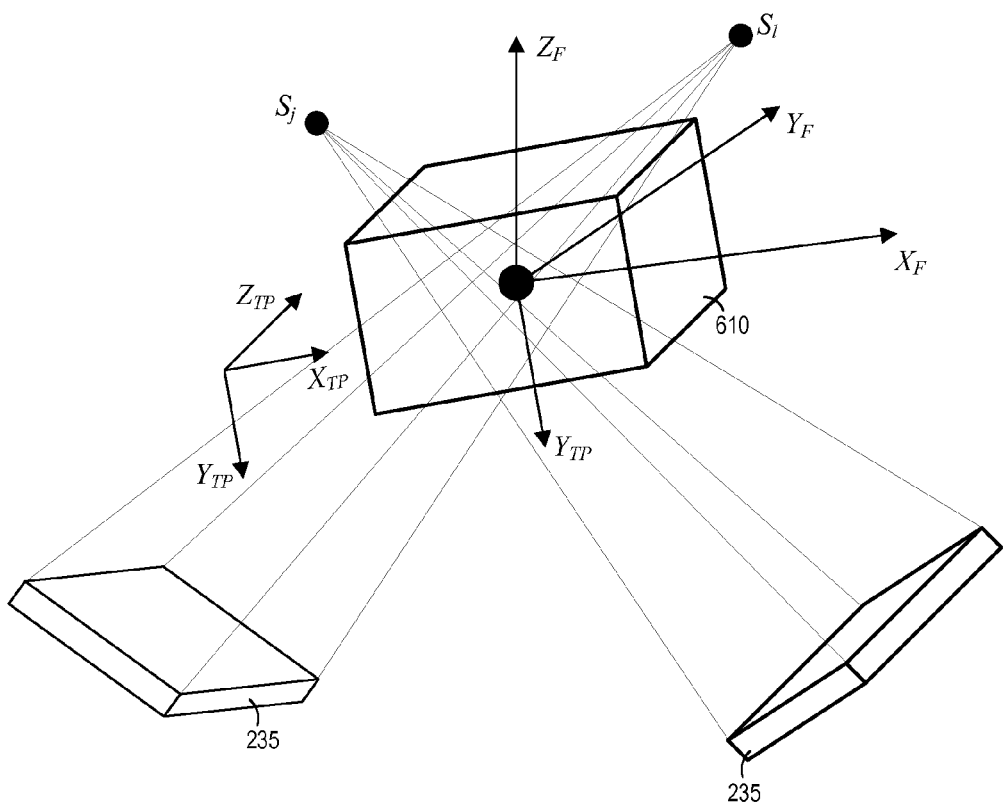
FIG. 6B illustrates acquisition of projection images according to some embodiments.

FIG. 6A illustrates three-dimensional pre-treatment image 600 acquired at S415 in coordinate system TP, and FIG. 6B illustrates acquisition of projection images at S420 according to some embodiments. As shown, multiple two-dimensional projection images of the patient are acquired from multiple pre-determined locations of the X-ray source and detector (e.g., imaging device 235). Each projection j, $1 \leq j \leq N$, is associated with known source location $S_j$ and a known detector location in the Fixed coordinate system.

For each projection j with a fixed source and fixed detector location in space, a 3×4 projection matrix (transformation) $P_j$ exists that uniquely maps any three-dimensional point in the Fixed system $(x_F, y_F, z_F)$ onto a two-dimensional point $(u_j, v_j)$ on the detector, such that:

$$\begin{bmatrix} \lambda u_j \\ \lambda v_j \\ \lambda \end{bmatrix} = P_j \begin{bmatrix} x_F \\ y_F \\ z_F \\ 1 \end{bmatrix}$$

The elements of the projection matrix $P_j$ can be obtained via geometry calibration which takes into account physical characteristics of room 200 (e.g., position of x-ray source(s), position of flat panel detector, panel tilt, panel sag, etc.), as is known in the context of cone beam geometry calibration. The coordinate of the source $S_j$ in the Fixed coordinate system can be obtained from the projection matrix $P_j = P_{j(3\times4)} = [M_{j(3\times3)}^{-1} n_{j(3\times1)}]$ as $S_j^F = -M_{j(3\times3)}^{-1} n_{j(3\times1)}$, where $I_j$, $1 \leq j \leq N$ denotes the j-th acquired portal image.

The transformation from the linac coordinate system (i.e., F) to the pre-treatment image coordinate system (i.e., TP) may be determined at S435 by an iterative 2D-3D registration process. To begin iteration, an initial estimate of the transformation is determined by assuming that the center of image 600 is the linac isocenter and that the axes of TP are parallel with the axes of F. Accordingly, the TP coordinate of the center of the volume is $$\vec{I}_{center} = POS\left(\frac{N_{width}}{2}, \frac{N_{height}}{2}, \frac{N_{slices}}{2}\right)$$

Using the equation for $T_{TP}^F$ noted above, an initial estimate of the transformation may be expressed as:

$$T_{TP}^{F(0)} = T(\vec{I}_{center}) T_{pat\_ori}^{HFS} R^c_X(-90°)$$

For iteration k, the jth source location may be expressed in the TP system as follows:

$$S_j^{TP(k)} = T_{TP}^{F(k)} S_j^F;$$

Therefore, at S425, DRRs may be obtained for each source location used to acquire a projection image by ray-tracing from the jth source location in the TP system through image 600. The resultant DRR is denoted as $D_j^{(k)}$.

At S430, different error metrics or similarity measures may be defined as a function of the acquired projection images and their corresponding DRRs. For example:

$$\Delta^{(k)} = f(I_1, D_1^{(k)}, \ldots, I_N, D_N^{(k)})$$

Based on the above measure, the transformation from the F system to the TP system is updated such that the measure will be reduced after the next iteration:

$$T_{TP}^{F(k+1)} = g(T_{TP}^{F(k)}, \Delta^{(k)})$$

The process stops after a certain number of iterations or if an error threshold is met. If k* is the final iteration, then the transformation from the F system to the TP system is $T_{TP}^{F(k^*)}$, and the position of the linac isocenter in the TP system is computed as:

$$\vec{I}_{TP} = T_{TP}^{F(k^*)} \begin{bmatrix} 0 \\ 0 \\ 0 \\ 1 \end{bmatrix}$$

Figure 7:
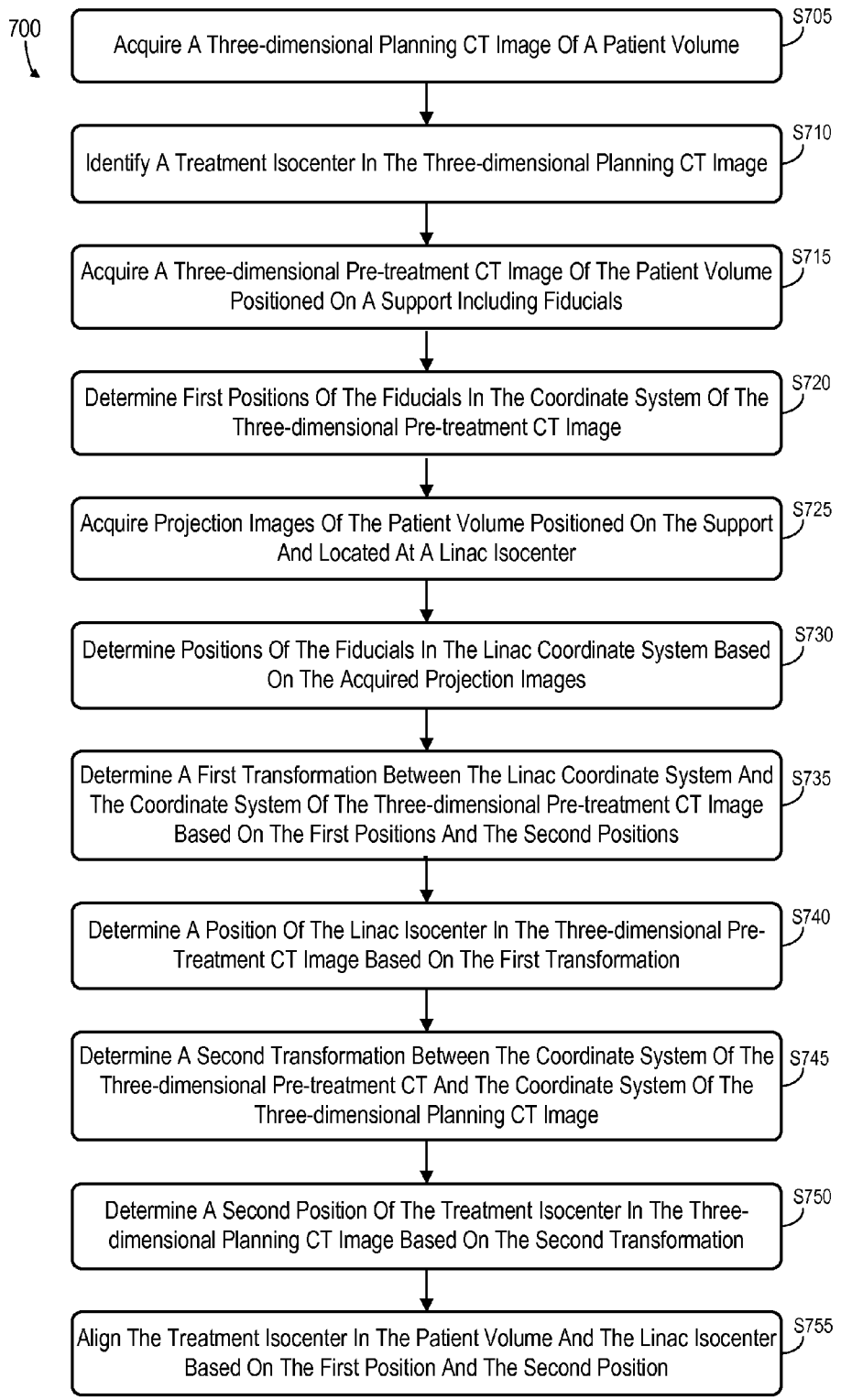
FIG. 7 comprises a flow diagram illustrating a process according to some embodiments.

FIG. 7 is a flow diagram of process 700 according to some embodiments. A three-dimensional planning image of a patient volume is initially acquired at S705. As described with respect to S405, the three-dimensional planning image may be acquired, for example, by using a CT scanner such as scanner 110, a kilovoltage or megavoltage cone beam imaging system, or by obtaining a three-dimensional planning image which was created by another entity in a computer-readable format.

A treatment isocenter in the three-dimensional planning CT image is identified at S710, and a treatment plan may also be determined at S710 based on the treatment isocenter. Next, and relatively soon before treatment, a three-dimensional pre-treatment image of the patient volume is acquired at S715. The three-dimensional pre-treatment image is acquired while the patient volume is positioned on a support including fiducials.

Figure 8:
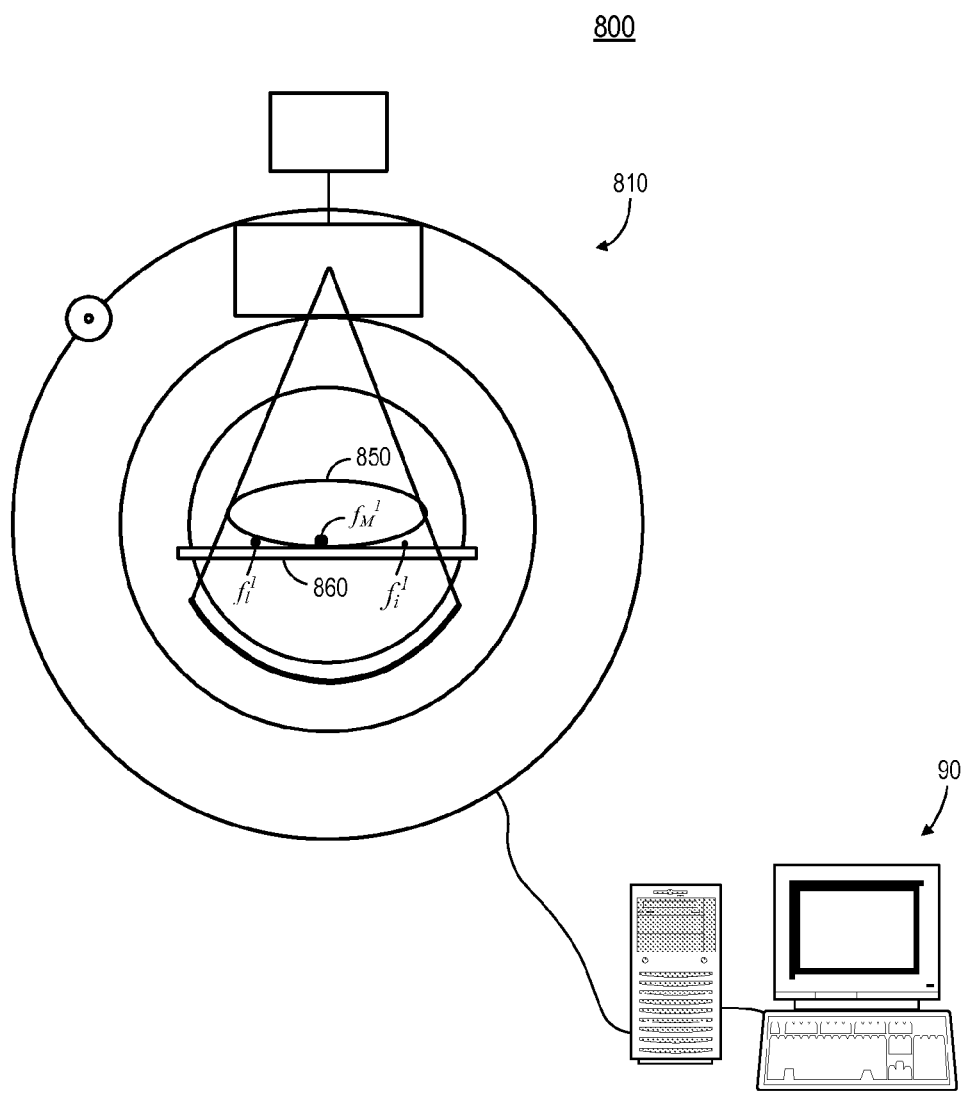
FIG. 8 illustrates a computed tomography system according to some embodiments.

FIG. 8 illustrates room 800 for executing some embodiments of S715. CT scanner 810 may operate as described above with respect to CT scanner 110. Support 860 may comprise a platform, a table, a couch, or any other system suitable for supporting patient 850.

Support 860 includes fiducials $f_l^1$, $f_M^1$, and $f_i^1$. Fiducials $f_l^1$, $f_M^1$, and $f_i^1$ may be permanently or removably attached to support 860 using any suitable attachment system. Fiducials $f_l^1$, $f_M^1$, and $f_i^1$ may be shaped, sized and/or arranged on support 860 in a manner which facilitates their individual identification within acquired images.

Fiducials $f_l^1$, $f_M^1$, and $f_i^1$ may be composed of any combination of materials which are compatible with megavoltage-based imaging. Since CT scanner 810 utilizes kilovoltage radiation, fiducials $f_l^1$, $f_M^1$, and $f_i^1$ and may also be compatible with kilovoltage-based imaging. Examples include oxides of transition metals such as aluminum oxide and zirconium oxide, which are visible in megavoltage images and do not create excessive streaking in kilovoltage images.

Accordingly, the image acquired at S715 will include the fiducials of support 860. Positions of the fiducials within the pre-treatment image are determined at S720. The positions are determined in the coordinate system of the pre-treatment image.

Next, at S725, the patient volume is moved to a linac isocenter and projection images of the patient volume are obtained. As described with respect to S420 of process 400, acquisition of the projection images may include rotating a gantry to various positions around a patient and, at each position, emitting radiation toward a detector to acquire a two-dimensional projection image of the patient. In contrast to S420, the projection images are acquired while the patient is positioned on support 860 including fiducials $f_1^1$, $f_M^1$, and $f_i^1$.

FIG. 9 illustrates treatment room 900 during acquisition of the projection images at S725. As shown, patient 850 is positioned on support 860, which includes fiducials $f_1^1$, $f_M^1$, and $f_i^1$. Accordingly, some, but not necessarily all, of the acquired projection images will include an image of a fiducial. Patient 850 may be positioned at S725 by aligning tattoo marks corresponding to the treatment isocenter with lasers (not shown) within treatment room 900.

Next, at S730, positions of the fiducials in the linac coordinate system are determined based on the acquired projection images. Briefly, the positions may be triangulated based on their positions within the projection images and the corresponding locations of imaging device 935 during acquisition of the projection images. A detailed description of the determination at S730 according to some embodiments is provided below.

A first transformation between the linac coordinate system and the coordinate system of the three-dimensional pre-treatment image is determined at S735. The first transformation is determined based on the positions determine at S720 and the positions determined at S730. Again, a detailed example of this determination is provided below.

Next, at S740, a position of the linac isocenter in the three-dimensional pre-treatment image is determined based on the first transformation. As mentioned above, the first transformation may be used to transform the origin (i.e., (0, 0, 0)) in the linac coordinate system to a corresponding point in the coordinate system of the three-dimensional pre-treatment image.

A second transformation between the coordinate system of the three-dimensional pre-treatment image and the coordinate system of the three-dimensional planning image is determined at S745. This transformation may comprise a feature-based 3D-3D registration between the two images as is known in the art. Based on second transformation, a position of the treatment isocenter in the three-dimensional pre-treatment image is determined at S750.

The position of the treatment isocenter in the three-dimensional pre-treatment image, and the position of the linac isocenter in the three-dimensional pre-treatment image are now known. The relative positions of the linac isocenter and the treatment isocenter, and without regard to coordinate systems, may therefore be easily determined therefrom. The treatment isocenter in the patient volume is aligned with the linac isocenter based on this determination at S755

The following is a detailed example of S730 through S740 according to some embodiments. As mentioned above, positions of fiducials in the linac coordinate system are determined at S730 based on the projection images acquired by the linac.

Figure 10A:
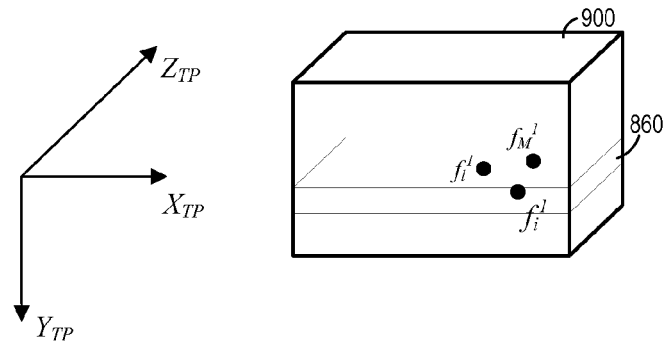
FIG. 10A illustrates a three-dimensional pre-treatment image according to some embodiments.
Figure 10B:
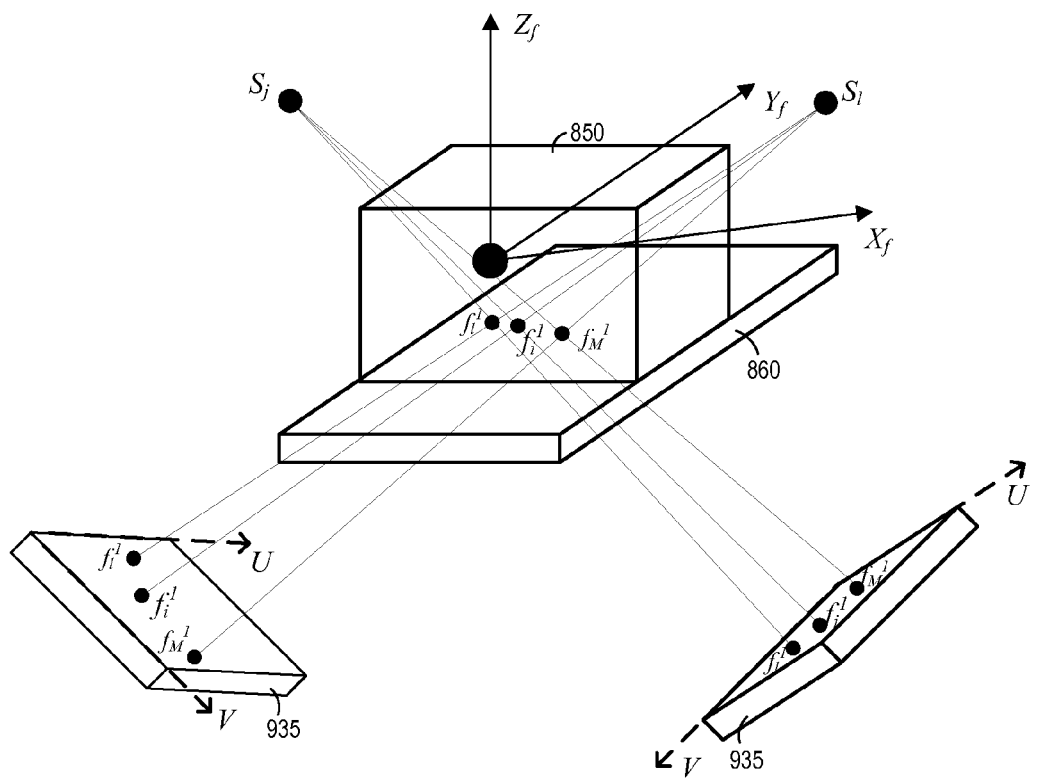
FIG. 10B illustrates acquisition of projection images according to some embodiments.

FIG. 10A illustrates pre-treatment image 900 and support 860 according to some embodiments. FIG. 10B illustrates the acquisition of two projection images of patient 850 while positioned on support 860. Each projection j, $1 \leq j \leq N$, is associated with known source location $S_j$ and a known detector location in the Fixed coordinate system. Moreover, as described above, for each projection j with a fixed source and fixed detector location in space, a transformation $P_j$ uniquely maps any three-dimensional point in the Fixed system ($x_F$, $y_F$, $z_F$) onto a two-dimensional point ($u_j$, $v_j$) on the detector.

Therefore, the three-dimensional coordinate $\vec{f}_i^F$ of a fiducial in the is F system is related to the two-dimensional coordinate in the j-th projection $\vec{f}_i^j$ via the projection matrix $P_j$. Specifically, $\vec{f}_i^j = P_j \vec{f}_i^F$.

Based on the foregoing, the following set a system of overdetermined linear equations holds for every unknown three-dimensional fiducial position $\vec{f}_i^F$.

$$\begin{bmatrix} \vec{f}_i^1 \\ \ldots \\ \vec{f}_i^j \\ \ldots \\ \vec{f}_i^N \end{bmatrix} = \begin{bmatrix} P_1 \\ \ldots \\ P_j \\ \ldots \\ P_N \end{bmatrix} \vec{f}_i^F$$

$\vec{f}_i^F$ is determined by solving the above set of equations. For each fiducial, its three-dimensional coordinate in the pre-treatment image (i.e., $\vec{f}_i^{TP}$) and its three-dimensional coordinate in the linac coordinate system (i.e., $\vec{f}_i^F$) are known.

The transformation $T_{TP}^F$ from the linac coordinate system to the pre-treatment image coordinate system may then be determined at S735 based on the following set of overdetermined set of linear equations:

$$\begin{bmatrix} \vec{f}_1^{TP} \\ \ldots \\ \vec{f}_i^{TP} \\ \ldots \\ \vec{f}_M^{TP} \end{bmatrix} = T_{TP}^F \begin{bmatrix} \vec{f}_1^F \\ \ldots \\ \vec{f}_i^F \\ \ldots \\ \vec{f}_M^F \end{bmatrix}$$

Next, at S740, the location $\vec{I}_{TP}$ of the linac isocenter in the TP system is determined based on $\vec{T}_{TP}^F$:

$$\vec{I}_{TP} = T_{TP}^F \begin{bmatrix} 0 \\ 0 \\ 0 \\ 1 \end{bmatrix}$$

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A method comprising:
    acquiring a first three-dimensional computed tomography image of a patient volume at a computed tomography scanner;
    acquiring projection images of the patient volume located at an isocenter of a linear accelerator;
    determining a first transformation between a coordinate system of the linear accelerator and a coordinate system of the first three-dimensional computed tomography image based on the projection images;
    acquiring a second three-dimensional computed tomography image of the patient volume;
    identifying a treatment isocenter in the second three-dimensional computed tomography image;
    determining a second transformation between the coordinate system of the first three-dimensional computed tomography image and the coordinate system of the second three-dimensional computed tomography image;
    determining a first position of the linac isocenter in the first three-dimensional computed tomography image based on the first transformation;
    determining a second position of the treatment isocenter in the first three-dimensional computed tomography image based on the second transformation; and
    aligning the treatment isocenter in the patient volume with the linac isocenter based on the first position and the second position.

2. A method according to claim 1, wherein determining the transformation comprises:
    for each acquired projection image, calculating a corresponding projection images from the first three-dimensional computed tomography image; and
    determining the transformation based on differences between the calculated projection images and their corresponding acquired projection images.

3. A method according to claim 1, wherein acquiring the first three-dimensional computed tomography image of the patient volume comprises:
    acquiring the first three-dimensional computed tomography image of the patient volume positioned on a support comprising fiducials,
    wherein acquiring projection images of the patient volume located at the isocenter of the linear accelerator comprises:
    acquiring projection images of the patient volume positioned on the support, and
    wherein determining the transformation comprises:
    determining first positions of the fiducials in the coordinate system of the first three-dimensional computed tomography image;
    determining second positions of the fiducials in the coordinate system of the linear accelerator based on the projection images; and
    determining the transformation based on the first positions and the second positions.

4. A non-transitory medium storing processor-executable program code, the program code executable to:
    acquire a first three-dimensional computed tomography image of a patient volume at a computed tomography scanner;
    acquire projection images of the patient volume located at an isocenter of a linear accelerator;
    determine a transformation between a coordinate system of the linear accelerator and a coordinate system of the first three-dimensional computed tomography image based on the projection images;
    acquire a second three-dimensional computed tomography image of the patient volume;
    identify a treatment isocenter in the second three-dimensional computed tomography image;
    determine a second transformation between the coordinate system of the first three-dimensional computed tomography image and the coordinate system of the second three-dimensional computed tomography image;
    determine a first position of the linac isocenter in the first three-dimensional computed tomography image based on the transformation;
    determine a second position of the treatment isocenter in the first three-dimensional computed tomography image based on the second transformation; and
    align the treatment isocenter in the patient volume with the linac isocenter based on the first position and the second position.

5. A medium according to claim 4, wherein determination of the transformation comprises:
    for each acquired projection image, calculation of a corresponding projection images from the first three-dimensional computed tomography image; and
    determination of the transformation based on differences between the calculated projection images and their corresponding acquired projection images.

6. A medium according to claim 4, wherein acquisition of the first three-dimensional computed tomography image of the patient volume comprises:
    acquisition of the first three-dimensional computed tomography image of the patient volume positioned on a support comprising fiducials,
    wherein acquisition of the projection images of the patient volume located at the isocenter of the linear accelerator comprises:
    acquisition of the projection images of the patient volume positioned on the support, and
    wherein determination of the transformation comprises:
    determination of first positions of the fiducials in the coordinate system of the first three-dimensional computed tomography image;
    determination of second positions of the fiducials in the coordinate system of the linear accelerator based on the projection images; and
    determination of the transformation based on the first positions and the second positions.

7. A system comprising:
    a computed tomography scanner to acquire a first three-dimensional computed tomography image of a patient volume;
    an imaging system to acquire projection images of the patient volume located at an isocenter of a linear accelerator; and
    a computing device to:
        determine a transformation between a coordinate system of the linear accelerator and a coordinate system of the first three-dimensional computed tomography image based on the projection images;
        identify a treatment isocenter in a second three-dimensional computed tomography image;
        determine a second transformation between the coordinate system of the first three-dimensional computed tomography image and the coordinate system of the second three-dimensional computed tomography image;

determine a first position of the linac isocenter in the first three-dimensional computed tomography image based on the transformation;

determine a second position of the treatment isocenter in the first three-dimensional computed tomography image based on the second transformation; and align the treatment isocenter in the patient volume with the linac isocenter based on the first position and the second position.

8. A system according to claim 7, wherein determination of the transformation comprises:

calculation, for each acquired projection image, of a corresponding projection image from the first three-dimensional computed tomography image; and determination of the transformation based on differences between the calculated projection images and their corresponding acquired projection images.

9. A system according to claim 7, further comprising:
a support comprising fiducials,
wherein acquisition of the first three-dimensional computed tomography image of the patient volume comprises:
acquisition of the first three-dimensional computed tomography image of the patient volume positioned on the support comprising fiducials,
wherein acquisition of the projection images of the patient volume located at the isocenter of the linear accelerator comprises:
acquisition of the projection images of the patient volume positioned on the support, and
wherein determination of the transformation comprises:
determination of first positions of the fiducials in the coordinate system of the first three-dimensional computed tomography image;
determination of second positions of the fiducials in the coordinate system of the linear accelerator based on the projection images; and
determination of the transformation based on the first positions and the second positions.

* * * * *